United States Patent [19]
Wall et al.

[11] Patent Number: 5,580,790
[45] Date of Patent: Dec. 3, 1996

[54] METHOD AND APPARATUS FOR PROCESSING FLUIDS

[75] Inventors: Robert Wall, Andover, Mass.; George H. Sierra, Goffstown; Robert Evans, Gilford, both of N.H.; Sarah Bazydola, Waltham, Mass.; Alan Polito, Danville, Calif.

[73] Assignee: Chiron Corporation, Emeryville, Calif.

[21] Appl. No.: 327,349

[22] Filed: Oct. 21, 1994

[51] Int. Cl.$^6$ .................................. G01N 21/07
[52] U.S. Cl. .................. 436/45; 436/46; 436/164; 436/165; 436/169; 436/177; 436/518; 436/528; 436/530; 422/58; 422/64; 422/72; 422/82.05; 422/101; 422/102; 422/104
[58] Field of Search .................. 436/45, 46, 164, 436/165, 169, 177, 518, 528, 530; 422/58, 64, 72, 82.05, 101, 102, 104; 435/973; 220/555, 631

[56] References Cited

U.S. PATENT DOCUMENTS

| | | | |
|---|---|---|---|
| 3,605,829 | 4/1970 | Genese et al. | 141/79 |
| 3,951,608 | 4/1976 | Trod | 422/64 |
| 4,239,853 | 12/1980 | Bradley | 422/72 |
| 4,314,970 | 2/1982 | Stein et al. | 422/72 |
| 4,373,812 | 2/1983 | Stein et al. | 422/72 |
| 4,387,164 | 6/1983 | Hevey et al. | 436/165 |
| 4,387,992 | 6/1983 | Swartz | 422/72 |
| 4,390,499 | 6/1983 | Curtis et al. | 422/72 |
| 4,456,581 | 6/1984 | Edelmann et al. | 422/72 |
| 4,580,897 | 4/1986 | Nelson et al. | 422/64 |
| 4,595,563 | 6/1986 | Degrave | 422/72 |
| 4,678,331 | 7/1987 | Perry | 356/246 |
| 4,735,502 | 4/1988 | Kaufmann | 356/246 |
| 4,777,141 | 10/1988 | Calzi et al. | 436/165 |
| 4,803,171 | 2/1989 | Baier et al. | 436/530 |
| 4,902,479 | 2/1990 | Brikos | 422/72 |
| 5,147,607 | 9/1992 | Mochida | 422/58 |
| 5,186,709 | 2/1993 | Hissung | 422/64 |
| 5,186,896 | 2/1993 | Bouchee et al. | 422/72 |
| 5,296,356 | 3/1994 | Mangold et al. | 435/7.92 |
| 5,300,423 | 4/1994 | Zoha et al. | 435/7.1 |
| 5,384,264 | 1/1995 | Chen et al. | 422/58 |

FOREIGN PATENT DOCUMENTS

0417305A1 3/1991 European Pat. Off. .

OTHER PUBLICATIONS

Abstracts of Japan, vol. 005, No. 100 (P-068), 27 Jun. 1981 and JP, A, 56 044852 (Hitachi), 24 Apr. 1981.

Primary Examiner—Lyle A. Alexander
Assistant Examiner—Sharidan Carrillo
Attorney, Agent, or Firm—Wolf, Greenfield & Sacks, P.C.

[57] ABSTRACT

Embodiments of the present invention feature a multichambered cuvette having a first movement pattern and a second movement pattern, the first movement pattern comprises a stationary position and a rotation about a circular path. The second movement pattern comprises a rocking motion. The cuvette uses the first movement of fluid between chambers and a second movement pattern to effect mixing and incubation. The cuvette features a unitary housing having an opening over the first and second compartments to allow viewing and access.

22 Claims, 2 Drawing Sheets

5,580,790

1

METHOD AND APPARATUS FOR PROCESSING FLUIDS

TECHNICAL FIELD

The invention relates to methods and apparatus for performing chemical or biological analyses of samples. One preferred embodiment of the present invention features a method and apparatus for performing immunological nucleic acid probe analyses in a vessel having a plurality of compartments. The compartments are in fluid communication upon rotation of the vessel.

BACKGROUND OF THE INVENTION

Affinity binding assays are often used to detect the presence of a molecule associated with a disease condition or biological state. These assays are based upon binding pairs, a pair of molecules which exhibit mutual affinity or binding capacity. Typically, one of the molecules of the binding pair is designated the ligand and one of the molecules of the binding pair is designated the antiligand, receptor, analyte or target. The designation is arbitrary in the sense that it depends on which molecule one wants to detect. The binding pair may comprise two complementary nucleic acids, antigens and antibodies, drugs and drug receptor sites, and enzymes and enzyme substrates.

Typically, one member of the biological binding pair is immobilized on a solid surface such as plastic, glass or nitrocellulose paper. A sample, potentially containing the molecule of interest, is applied to the solid support. After a period of incubation, in which the molecule of interest has an opportunity to bind to the immobilized ligand, the unbound sample is removed. During this period of incubation the sample and support are rocked to create a current of fluid over the support to maximize the opportunity of target molecules to be received by the immobilized ligand. The target, if present, forms a complex with the immobilized ligand.

Next, additional reagents are applied to the support which reagents are capable of reacting with the complex formed or the target captured by the immobilized ligand. These further reagents typically includes a labeled second ligand, which second ligand is capable of binding to the target or the complex. A labeled second ligand has a label, a molecular moiety capable of detection. Typical labels include by way of example, without limitation, radioactive isotopes, enzymes, luminescent agents, precipitating agents and dyes.

The support is monitored in the presence of appropriate signal generating conditions for the presence of signal. The signal is indicative of the presence of the target.

Methods to immobilize immunological agents, peptides and nucleic acid on a solid support are well known in the art. Nucleic acid sequences specific for a particular disease state are commonly reported in the scientific press, U.S. and foreign patents and published applications and various databank for nucleic acid sequence information. Immunological agents such as antibodies specific for a particular organism or disease states are also reported in the scientific press, U.S. and foreign patents and published patent applications, scientific catalogs of chemical suppliers (such as Sigma Chemical Company of St. Louis, Mo., U.S.A.), and with respect to cell-lines maintained by depositories (such as The American Type Culture Collection of Rockville, Md., U.S.A.).

2

The performance of affinity assays has been limited due to the need to manually apply and remove reagents to detect the presence of the analyte. Affinity assays are typically performed in cuvettes, small test tube-like vessels. The small volumes and openings of cuvettes are awkward and can lead to operator error.

Although aspects of the process have been automated, there remains a need for a containment vessel that allows substantially the entire assay to be run in an automated fashion. There remains a need for a vessel to facilitate the application and removal of fluids and to permit the incubation of the sample and immobilized ligands in a consistent manner.

SUMMARY OF THE INVENTION

The present invention features methods and device for handling small controlled volumes of fluids. The methods and devices of the present invention are ideally suited for performing affinity binding assays.

One embodiment of the present invention features a vessel for processing fluids. The vessel processes fluids by moving in a first movement pattern. The first movement pattern comprises a stationary position and rotation in a circle. The circle has an axis, radius and a plane of rotation. As used herein, the term "axially" means towards the axis. The term "peripheral" refers to the periphery of the plane of rotation, or the edge of the circle at its greatest arc. Rotation is of the type associated with turntables and centrifuges to impart centrifugal force of fluids held in the vessel.

The vessel comprises a housing having a chamber. The chamber has a first compartment and a second compartment. The first compartment has one or more walls defining a cavity for holding a fluid. Similarly, the second compartment has one or more walls defining a cavity for holding a fluid. At least one of the one or more walls of the first compartment and at least one of the one or more walls of the second compartment comprise weir means. Weir means are interposed between the first and second compartment to define a fluid retention area in the first compartment for holding liquid when the vessel is in a stationary position and a passage within the chamber for fluids while the housing is rotating in the first movement pattern. The passage is in fluid communication with the first and second compartment upon rotation of the housing. The second compartment has at least one of said one or more walls defining a second fluid retention area for holding fluid when the vessel is in a stationary position and at least a third fluid retention area when the housing is rotated. The vessel receives fluid in the first compartment and releases the fluid from the first compartment, upon rotation of the housing by centrifugal force through the passage, and into the second compartment. The fluid received in the second compartment upon rotation is held in the third fluid retention area. The fluid received in the second compartment is held in the second fluid retention area in the stationary position.

Preferably, the second fluid retention area of the second compartment has a bottom surface having a depression for receiving fluids. The depression facilitates removal of fluids by a pipette or other means.

Preferably, the vessel has weir means comprising at least one fluid transporting surface. The fluid transporting surface is inclined to receive fluids from the first fluid retention area and transport such fluid via a centrifugal force. The fluid transporting surface preferably has an angle with respect to the plane of rotation, measured from within the chamber from the plane of rotation to such surface, which angle is greater than 90°. Measurements with respect to the plane of rotation are in reference to such plane extending approximately parallel to the bottom of the vessel.

Preferably, the first compartment has at least one wall for receiving a test strip. Preferably, the wall is flat, planar and at the bottom of the first compartment in order to receive fluid over its entire surface. Preferably, the test strip has a member of a binding pair immobilized upon an upper surface. A preferred member of a binding pair comprises immunological or nucleic acid probes. Typical immunological probes comprise antibodies and antigens associated with a disease state or a biological condition. Typical nucleic acid probe reagents comprise a nucleic acid having a nucleotide sequence capable of hybridizing to a target nucleic acid. The target nucleic acid is typically associated with a disease state or a biological condition.

Preferably, the housing further comprises pivoting means for imparting a second movement pattern to the housing. The second movement pattern preferably comprises a rocking motion for mixing fluids within the first or second compartment during an incubation process.

A preferred pivoting means comprises tabs projecting from the housing about the first compartment. The tabs are capable of being received in supporting notches allowing rotation of the housing upon a pivoting arc. A preferred pivoting arc is up to 30°. That is, the pivoting arc where the pivot point is between the axial end and the peripheral end of the device is up to 15° above or below the plane of rotation.

The present housing is preferably adapted to be held on a turntable. A preferred turntable has notches for receiving tabs projecting from the housing. Thus, the turntable is capable of imparting a first movement pattern to the housing. The tabs projecting from the housing are received in notches to allow the housing to assume a second movement pattern. Preferably, the notches and tabs cooperate to center the vessel, or maintain the position of the vessel, as the vessel is rocked.

Preferably, the turntable has means for imparting the second movement pattern. One embodiment of the present invention features a housing having arm means for engaging a second movement pattern means. A preferred second movement pattern means comprises a reciprocating hub capable of reciprocating vertical movement. The housing has an arm for engaging the hub to rock the housing in a pivoting motion.

Preferably, the first compartment is capable of receiving light and has one or more walls having a light diffusing surface. In the alternative, the one or more walls may have a light absorbing surface in order to provide consistent illumination of the first compartment. Preferably, the first compartment comprises a test strip which is read by illumination.

Preferably, at least one of the one or more walls of the first compartment comprising weir means is inclined to allow light to enter the first compartment to illuminate the bottom planar surface. The one or more walls have an angle with respect to the plane of rotation, which angle, measured from within the chamber from the plane of rotation to such wall, is preferably greater than 90°, and most preferably within a range of angles of 110°–165°, and, most preferably, approximately 120°.

Preferably, the first compartment has a bottom planar surface. Preferably, the bottom planar surface has immobilized immunological or nucleic acid probes or is capable of receiving one or more test strips containing immunological or nucleic acid probes.

Preferably, the first compartment further comprises two lateral walls, an axial wall and a weir wall. The weir wall forms part of the weir means, opposite the axial wall. Preferably, the two lateral walls have an angle with respect to the bottom planar wall which angle is substantially equal to provide a symmetrical reflective lighting pattern. Preferably, the angle of each lateral wall from the bottom planar surface is 90° or greater. More preferably, 90°–135°, and most preferably, approximately 95°.

Preferably, the axial wall and the weir wall have an angle with respect to the bottom wall which angle is substantially equal to provide a symmetrical reflective lighting pattern on the bottom wall. Preferably, the axial wall and the weir wall have an angle with respect to the bottom planar surface, measured from within the chamber from the bottom planar surface to each respective wall, which angle is greater than 90°, and, more preferably, 110°–165°, and most preferably, approximately 120°.

Preferably, at least one or more walls of the second compartment comprises weir means, a bottom wall, and a back wall. Preferably, the second compartment has a back wall which is axially inclined with respect the plane of rotation in order to form a third fluid retaining area. That is, the back wall has an angle, measured from within the chamber from the plane of rotation to such wall, which angle is less than 90°, and more preferably, 60°–70°.

Preferably, the one or more walls comprise a depression defining a low point within the second fluid retaining area. The depression drains fluid as such fluids are withdrawn by pipettes and the like.

Preferably, the vessel of the present invention is molded as a single unit providing ease of manufacture. The vessel may be preloaded with a test strip or adopted to receive a test strip to be placed by the operator. The vessel features a substantially open top. That is, the housing has an opening extending from the axial wall of the first compartment to the back wall of the second compartment.

A further embodiment of the present invention features a method of processing fluids. The method comprises placing a sample in a vessel for processing fluids by moving in a first movement pattern. As used herein, the term "sample" refers to a fluid which will undergo processing. In an analytical or diagnostic sense, the sample potentially contains an analyte. The vessel comprises a housing having a chamber having a first compartment and a second compartment. The first compartment has one or more walls defining a cavity for holding a liquid. Similarly, the second compartment has one or more walls defining a cavity for holding a fluid. At least one of the one or more walls of the first compartment and at least one of the one or more walls of the second compartment comprises weir means interposed between the first and second compartment defining a fluid retention area in the first compartment to hold liquid when the vessel is in a stationary position and a passage within the chamber for fluids. The second compartment has at least one or more walls defining a second fluid retention area for holding fluids when the vessel is in a stationary position and a third fluid retention area when the housing is rotated. The passage is in fluid communication with the first and second compartment upon rotation of the housing. The sample in the first compartment is processed and released into the second housing upon rotation of the housing and passage of the fluid through the passage into the second chamber compartment.

Embodiments of the present invention are ideally suited for the processing of test strips. Preferably, a single test strip is received within the first compartment of the vessel. The expansive, open chamber, open from the axial wall of the first compartment to the back wall of the second chamber, allows test strips to be easily read. The present invention is ideally suited for colorimetric evaluation of test strips in the form of an immunoblot assay. The open chamber further allows manual or automated pipettes of fluids into or out of the chamber.

Other features and advantages of the present invention will be apparent upon viewing the drawings and understanding the detailed description which follows.

DETAILED DESCRIPTION OF THE DRAWINGS

The method and apparatus of the present invention will be described in detail with respect to preferred embodiments featuring affinity binding assays. The focus of the description is not intended to be limiting but to highlight features and advantages of the invention. Indeed, the method and apparatus have applications in any situation in which multicompartment vessels capable of being rotated and pivoted may be useful.

Figure 1:
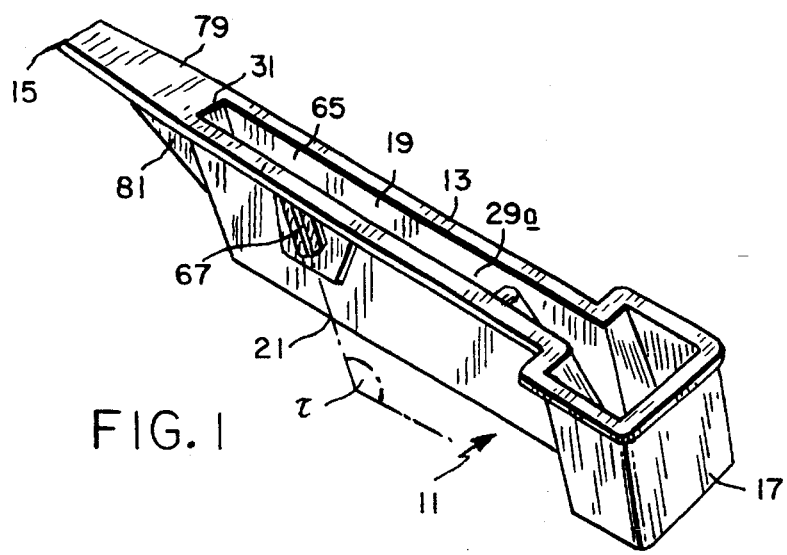
FIG. 1 is an isometric view of a device embodying features of the present invention.

Turning now to FIG. 1, a vessel for processing fluids, generally designated by the numeral 11, is depicted. Vessel 11 comprises a housing 13 capable of movement in two movement patterns.

Figure 2:
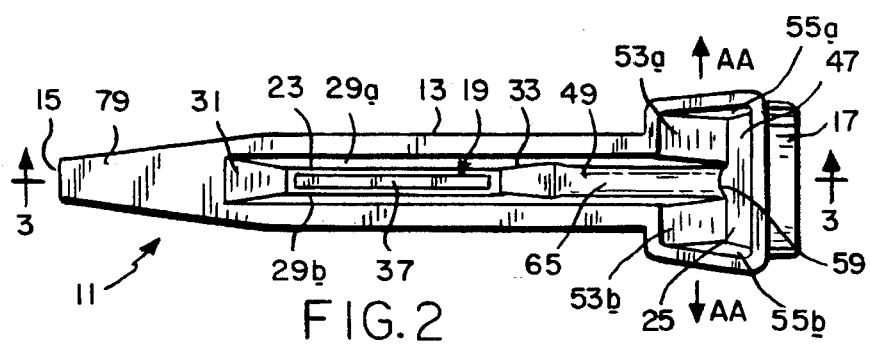
FIG. 2 is a plan view of the device illustrated in FIG. 1.

Turning now to FIG. 2, the first movement pattern comprises a stationary position and rotation in a circle. The circle has an axis, radius and a plane of rotation.

Housing 13 has an axial end 15 peripheral end 17. The axial end is placed towards the axis. The peripheral end 17 defines the periphery of the circle. The first movement pattern and the plane of rotation is suggested by the direction of heavy arrows AA. Measurements of angles with respect to such plane of rotation are with respect to such plane defined by the bottom of housing.

Figure 3:
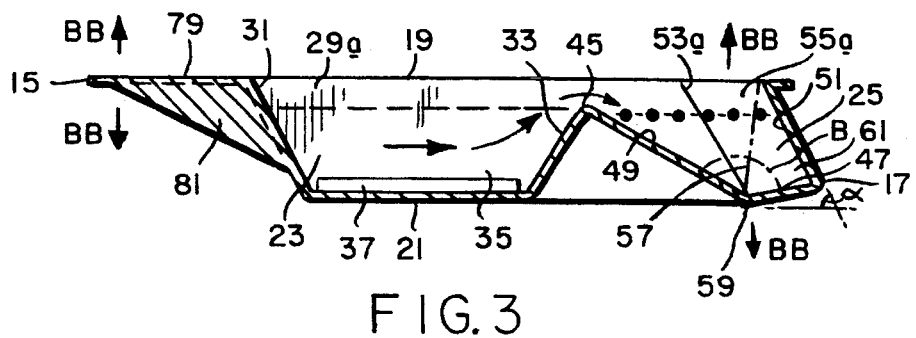
FIG. 3 is a sectional view of a device embodying features of the present invention, as viewed through lines 3—3 of FIG. 2.

Turning now to FIG. 3, housing 13 has a second movement pattern comprising a stationary position and rocking motion. The rocking motion comprising a pivoting movement about a point along the radius to tilt or incline the housing 13 with respect to the plane of rotation. In the situation where the pivot point is between the axial end 15 and the peripheral end 17, the second movement pattern is suggested by heavy arrows BB.

Housing 13 has one or more walls defining an inner chamber 19, as best seen in FIG. 2, and an exterior surface 21, best seen in FIG. 1. Housing 13 is preferably molded as a single unit.

Turning now to FIGS. 2 and 3, inner chamber 19 has a first compartment 23 and a second compartment 25. First compartment 23 has an axial position with respect to second compartment 25. First compartment 23 is defined by bottom wall 27, lateral walls 29a and b, axial wall 31 and weir wall 33. Preferably, the bottom wall 27 of the first compartment 23 is approximately 1.45 inches by 0.215 inches. Lateral walls 29 and b are approximately 0.85 inches in height. First compartment has a fluid retention area 35, indicated with dashed lines, for containing fluid while the housing 13 is stationary with respect to the first movement pattern and while rocking in the second movement pattern. The first compartment 23 may preferably contain fluid volumes of up to 1.8 ml.

The bottom wall 27 has a test strip 37 containing one or more biological binding agents. A preferred test strip is an immunological test strip. The present device is ideally suited for processing a CHIRON® RIBA™ Strip Immunoblot Assay (SIA) test strip.

Individuals skilled in the art will recognize that many types of antigens can be immobilized on a test strip to detect antibodies to such antigens. Individuals skilled in the art will further recognize that antibodies can be immobilized on a test strip by conventional means to detect different antigenic molecules. Antigen and antibody binding pairs are readily identified and components can be purchased from chemical supply companies, such as ICN Biomedicals, Inc., Irvine, Calif., U.S.A.

The examples of antibodies and antigens available from chemical supply companies are not intended to be limiting. Other antibodies and antigens can be readily identified and immobilized onto test strips 37.

Test strip 37 can be made with nucleic acid having a sequence capable of hybridizing to a target sequence. This sequence, a probe sequence, can be readily synthesized and affixed to a test strip by conventional means. The probe sequence can be obtained from any number of data banks such as GenBank®. The probe sequence is generally 10–20 nucleotides in length comprising sequences with the desired selectivity for the target.

The test strip 37 may comprise any solid support. Preferably, the test strip is nitrocellulose to retain colorimetric reaction products.

Figure 4:
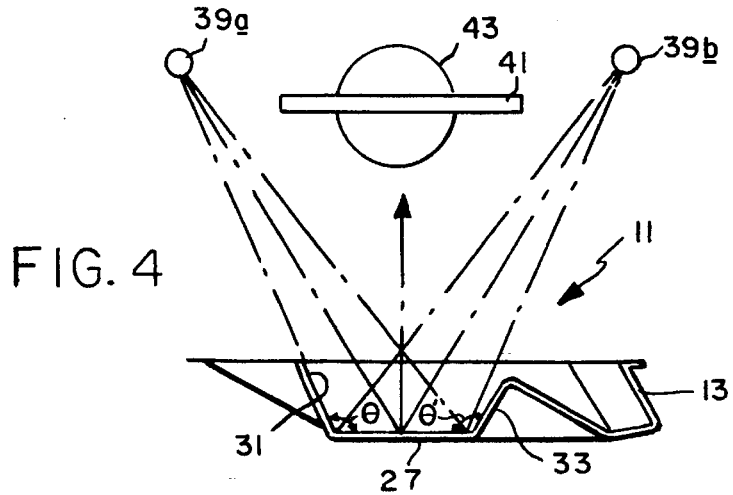
FIG. 4 is a cross-sectional view of a device embodying features of the present invention cooperating with illumination means and reading means.

First compartment 23 has optical properties to allow consistent reading of the test strip 37. Turning now to FIG. 4, axial wall 31 and weir wall 33 have an angle of incidence with respect to the plane of rotation and bottom wall 27. The angle $\theta'$ of weir wall 33, measured from bottom wall 27 up through chamber 19 to axial wall 31, and the angle $\theta$, measured from bottom wall 27 up through chamber 19 to axial wall 31, are approximately equal. A preferred angle $\theta$ and $\theta'$ is between 110°–165° and, most preferably, about 120°.

Similarly, lateral walls 29a and b have angles of incidence with respect to the plane of rotation and bottom wall 27. The angles of lateral wall 29a and b, measured from bottom wall 27 up to lateral wall 19a or b, are approximately equal. A preferred angle is 90°–135° and, most preferably, approximately 95°.

Lateral walls 29a and b, axial wall 31 and weir wall 33 reflect light, originating from a position above a line extending from axial wall 31 and weir wall 33, consistently to bottom wall 27. FIG. 4 illustrates illumination of bottom wall 27 by two light emission sources 39a and b. Light emission sources 39a and b produce light to illuminate bottom wall 27. The light originates from a position above a line extending from axial wall 31 and weir wall 33 to allow reading means to receive light reflected from bottom wall 27. Light reflected from bottom wall 27 is received by a prism 41 and camera 43 for evaluation or recording.

Lateral walls 29a and b, defining the first compartment 23, and axial wall 31 and weir wall 33 are preferably opaque or translucent in order to absorb or reflect light in a diffuse manner to facilitate reading of the test strip 37. Lateral walls 29a and b, axial wall 31 and weir wall 33 are blackened with pigments during a molding process or, preferably, lateral wall 29a and b, axial wall 31 and weir wall 33 have a consistent color and a matte or textured finish [not shown] for diffusing light.

Turning now to FIGS. 2 and 3, the angle of weir wall 33 with respect to bottom wall 27 and the plane of rotation facilitates the movement of fluids, from the first component to the second compartment, upon rotation of housing 13. Weir wall 33 has a height less than lateral walls 29a and b to define a passage 45 within inner chamber 19 in communication with second compartment 25. That is, when lateral walls 29a and b are 0.85 inches, a prepared height of weir wall 33 is 0.63 inches.

Second compartment 25 is defined by a bottom wall 47, forward wall 49, lateral walls 29a and b, back wall 51, projecting walls 53a and b and side walls 55a and b. Preferably the bottom wall 47 of second compartment 25 is approximately 1.1 inches by 0.4 inches. The lateral walls 29a and b are approximately 0.85 inches in height.

Second compartment 25 has two fluid retention areas in addition to the first fluid retention area 35 of the first compartment 23. A second fluid retaining area 57 is defined by bottom wall 47, forward wall 49, lateral walls 29a and b, back wall 51, projecting walls 53a and b and side walls 55a and b. Second fluid retention area 57, is suggested by a dotted line, as best seen in FIG. 3. Second fluid retention area 57 holds fluids in the second compartment 25 when the housing 13 is in the stationary position with respect to the first movement pattern.

Second retention area 57 has a depression 59 where axial wall 49 meets bottom wall 47. Depression 59 is capable of receiving pipettes and other fluid withdrawing devices [not shown] for removing fluid from second compartment 25.

A third fluid retention area 61 is defined substantially by bottom wall 47, back wall 51 and side walls 55a and b. Third fluid retention area 61, indicated with a dashed line, holds fluid in the second compartment 25 when the housing 13 is moving in the first movement pattern.

Individuals skilled in the art will readily recognize that the first, second and third retention areas 35, 37 and 61 change shape with the rotational of the housing 13 and volume of fluids which are held in each compartment. The second and third fluid retention areas are preferably sized to contain up to approximately 2.4 ml.

Sidewalls 55a and b and back wall 47 project laterally outward from lateral walls 29a and b to provide third retention area 61 with greater capacity. Back wall 47 is inclined with respect to the plane of rotation. Preferably, back wall 47 defines an angle α with respect to the plane of rotation. Angle α, measured from the plane of rotation to back wall 47 inside chamber 19, is approximately 60° to 75°. This angle α cooperates with a first movement pattern in a circle with a 5–12 inch radius and a speed of rotation of approximately 100–200 rpm. A preferred speed is approximately 160 rpm for a housing 13 of approximately 5 inches in total length and a circle of rotation of approximately 7 inches in radius.

Forward wall 49 of the second compartment 25 is inclined with respect to the plane of rotation to define angle β. Angle β, measured from the plane of rotation to forward wall 49 within chamber 19, is greater than 90° and, preferably, approximately 150°. Forward wall 49 receives fluid from passage 45 and transports fluid by centrifugal force, with minimum aerosol formation into the second compartment 25. Fluid moving upon forward wall 49 is maintained on the wall by surface tension or capillary action. Preferably, the surface of bottom wall 47, axial wall 31, lateral walls 29*a* and *b* within the second compartment 25, back wall 51, projecting walls 53*a* and *b* and sidewalls 55*a* and *b* are polished to facilitate fluid movement.

Axial wall 31, back wall 51, sidewalls 55*a* and *b*, projecting walls 53*a* and *b* and lateral walls 29*a* and *b* define an opening, generally designated by numeral 65. Opening 65, extending substantially the length of chamber 19, allows pipettes and other fluid dispensing and fluid withdrawing tools to be inserted into the first compartment 23 or second compartment 25 of chamber 19. Opening 65 allows the insertion of test strips 37 into the first compartment 23 or second compartment 25.

Returning now to FIG. 1, housing 13 has tabs 67 extending laterally outward from the exterior surface 21. Tabs 67 define a pivot point for imparting a rocking motion on housing 13.

Preferably, tabs 67 cooperate and are received in a supporting cradle 69 of a rotatable turntable 75, as best seen in FIG. 5. The bottom of tab 67 forms a pivot point midway the length of the first compartment 23. Turntable 75 is capable of movement in the first movement pattern to impart rotation to housing 13. Tabs 67 extent linearly from the top of housing to approximately the midpoint of exterior surface 21, to define a line with respect to the plane of rotation, and an angle $\tau$ will respect to the plane of rotation. Angle $\tau$, measured from the plane of rotation from the bottom of tabs 67, axially, to the top of tab 67, is 90° or greater such that tabs 67 tend to be retained in cradle 69 upon rotation.

Preferably, housing 13 has an arm 79. Arm 79 has a support 81 to provide rigidity. Arm 79 is capable of engaging vertical movement means for imposing the second movement pattern on housing 13. The tab 67, midpoint the length of the first compartment 23, define a pivot point with greater weight towards the peripheral end 17 of device 11. Thus, arm 79 need only to engage vertical movement means on an upper surface of arm 79. Preferably, vertical movement means comprise a vertically reciprocating hub 85 integral with turntable 75, as best seen in FIG. 6. As hub 85 moves up and down, arm 79 is compelled downward by the force of the hub and upward by the weight of the device 11 towards the peripheral end 17, to pivot housing 13 in cradle 69. A typical second movement pattern is approximately 10–30 inches per minute and preferably 16–20 cycles per minute.

The operation of the present device will be described with respect to a preferred embodiment in which the device carries a test strip 37 comprising a CHIRON® RIBA™ HCV 3.0 strip immunoblot assay. Other test strips 37 can be sized to fit the bottom surface 27 of the first compartment 23.

The CHIRON® RIBA™ HCV 3.0 strip immunoblot assay comprises the components identified in Table 1.

Table 1

Component Description

1. Hepatitis C Virus (HCV) Encoded Antigen/Peptide (Recombinant c33c and NS5, Synthetic 5-1-1p, c100p, and c22p) Coated Strips: each strip contains four individual bands coated with HCV-encoded antigens/peptides, a recombinant human SOD band, and two IgG control bands.
2. Specimen Diluent: phosphate-buffered saline (PBS) with bovine protein stabilizers and detergents. Contains 0.1% sodium azide and 0.05% gentamicin sulfate as preservatives.
3. Conjugate: peroxidase-labeled goat anti-human IgG (heavy and light chains), with bovine protein stabilizers. Contains 0.01T thimerosal as a preservative.
4. Substrate Solution: 4-chloro-1-naphthol in methanol.
5. Substrate Buffer: phosphate-buffered hydrogen peroxide.
6. Wash Buffer Concentrate (50×): phosphate buffered detergent solution containing 0.01% thimerosal as a preservative.
7. Positive Control (Human): inactivated human serum or plasma containing antibodies to HCV (anti-HCV) and nonreactive for hepatitis B surface antigen (HBsAg) and antibodies to human immunodeficiency virus type 1 (anti-HIV-1) and type 2 (anti-HIV-2). Contains 0.1% sodium azide and 0.05% gentamicin sulfate as preservatives.
8. Negative Control (Human): human serum or plasma nonreactive for HBsAg, anti-HIV-1, anti-HIV-2, and anti-HCV. Contains 0.1% sodium azide and 0.05% gentamicin sulfate as preservative.

Reagents are prepared according to the package insert.

Turning now to FIG. 3, a test strip 37 is affixed to the bottom surface 27 of the first compartment 23. In the event the assay is not intended to be run immediately, the device 11 is maintained under refrigeration. Approximately 30 minutes before beginning the assay, the device is removed from refrigeration and allowed to come to room temperature.

Figure 5:
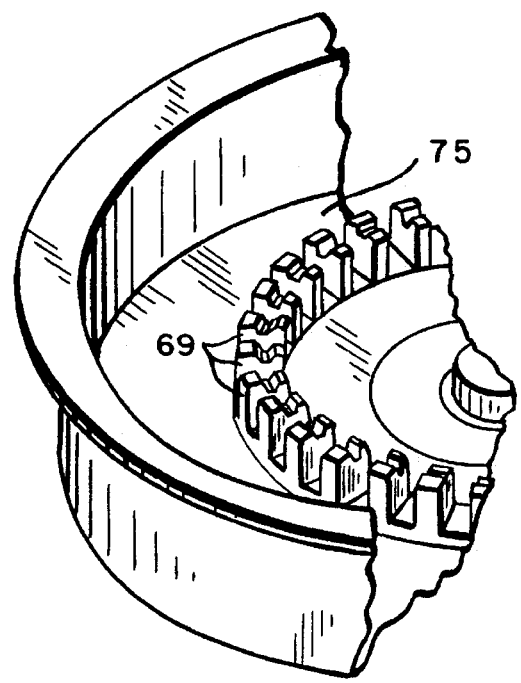
FIG. 5 depicts a turntable equipped with projecting notches for receiving the device depicted in FIG. 1.
Figure 6:
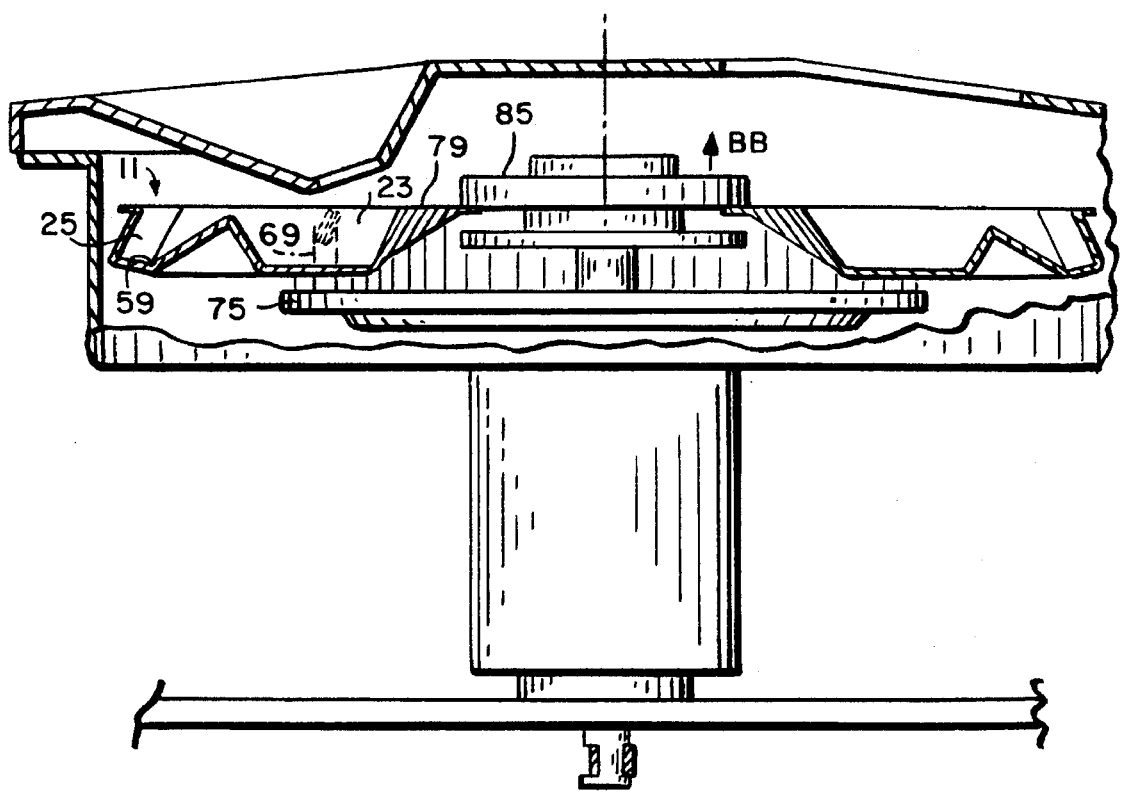
FIG. 6 is a turntable and a central hub assembly for imparting two movement patterns on the device embodying features of the present invention.

As shown in FIGS. 5 and 6, the device 11 is placed with tabs 67 nesting in cradle 69 of turntable 75. Arm 79 engages hub 85.

Approximately 0.5–2.0 ml of specimen diluent is added to the first compartment 23 of device 11. A preferred fluid volume, other than for specimens or controls is 1 ml. The vertically reciprocating hub 85 is activated to rock the device 11 to ensure that the entire strip is covered with liquid. The reciprocating hub 85 operates at 16 to 20 cylces per minute.

After the rocking motion is discontinued, approximately 20–40 microliters of the appropriate specimen or control are added to the first compartment 23 and the vertically reciprocating hub 85 is activated to rock the device 110 This second movement pattern will continue for 4–4½ hours.

Next, the turntable 75 is activated into a first movement pattern, rotating the device 11. Fluid contained in the first compartment 23 travels up weir wall 33 and through the passage 45 and into the second compartment 25. Fluid is maintained in the third fluid retention area 61 of second compartment 25 by centripetal force. The rotation of turntable 75 is stopped and fluid assumes a position in second fluid retention area 57 of second compartment 25. Fluid in the second fluid rotation area 57 is withdrawn by a pipette entering the second compartment 25 and operating from depression 59.

Next, a further 0.5–2.0 ml of specimen diluent is added to the first compartment 23 of a device 11. Again, the vertical reciprocating hub 85 is activated into the second movement pattern. Device 11 is rocked about tabs 67 for approximately 30 minutes at room temperature.

Next, the turntable 75 is once again activated in a first movement pattern. The rotation propels fluid held in the first compartment 23 of device 11 up weir wall 33, through passage 45, and into the second compartment 25. Fluid is maintained in the third fluid retention area 61 of second compartment 25 by centripetal force. The rotation of turntable 75 is stopped and fluid assumes a position in second fluid retention area 57 of second compartment 25. Fluid in the second fluid rotation area 57 is withdrawn by a pipette entering the second compartment 25 and operating from depression 59.

Next, 0.5–2.0 ml of working wash buffer (2×) is placed in the first compartment 23. The vertical reciprocating hub 85 is once again activated for a short period of time, to impart a rocking motion to the device 11.

Thereafter, the turntable 75 is activated in a first movement pattern to rotate. The rotation propels the working wash buffer in the first compartment 23 up weir wall 33, through passage 45, and into the second compartment 25. Fluid is maintained in the third fluid retention area 61 of second compartment 25 by centripetal force. The rotation of turntable 75 is stopped and fluid assumes a position in second fluid retention area 57 of second compartment 25. Fluid in the second fluid retention area 57 is withdrawn by pipettes entering the second compartment 25 and operating from depression 59. The step of adding and removing working wash buffer may be repeated.

Next, 0.5–2.0 ml of conjugate solution is placed in the first compartment 23. Again, the vertical reciprocating hub 85 is activated to impart a rocking motion to the device 11 and maintained for 10 minutes.

The conjugate solution is removed from the first compartment 23 by imposing the first movement pattern on device 11 by activating turntable 75. The conjugate solution, held in first compartment 23, is propelled by centrifugal force up weir wall 33, through passage 45 and into the second compartment 25. Fluid is maintained in the third fluid retention area 61 of second compartment 25 by centripetal force. Rotation of turntable 75 is stopped and fluid assumes a position in second fluid retention area 57 of second compartment 25. Fluid in the second fluid retention area 57 is withdrawn by a pipette entering the second compartment 25 and operating from depression 59.

Next, 0.5–2.0 ml of working wash buffer (3×) is placed in the first compartment 23. The vertical reciprocating hub 85 is once again activated for a short period of time, to impart a rocking motion to the device 11.

Thereafter, the turntable 75 is activated in a first movement pattern to rotate. The rotation propels the working wash buffer in the first compartment 23 up weir wall 33, through passage 45, and into the second compartment 25. Fluid is maintained in the third fluid retention area 61 of second compartment 25 by centripetal force. The rotation of turntable 75 is stopped and fluid assumes a position in second fluid retention area 57 of second compartment 25. Fluid in the second fluid retention area 57 is withdrawn by a pipette entering the second compartment 25 and operating from depression 59. The step of adding and removing working wash buffer may be repeated.

Next, 0.5–2.0 ml of working substrate solution is then added to the first compartment 23 and again the vertical reciprocating hub 85 is activated to impart a second movement pattern on the device 11. Device 11 is rocked for 15 minutes.

The working substrate solution is removed from the test strip 27 held in first compartment 23 by activating the turntable 75 into a first movement pattern. The working substrate solution held in first compartment 23 is propelled by centrifugal force up weir wall 33, through passage 45, and into the second compartment. Fluid is maintained in the third fluid retention area 61 of second compartment 25 by centripetal force. The rotation of turntable 75 is stopped and fluid assumes a position in second fluid retention area 57 of second compartment 25. Fluid in the second fluid retention area 57 is withdrawn by a pipette entering the second compartment 25 and operating from depression 59.

Next, 0.5–2.0 ml of deionized water is placed in first compartment 23. The vertical reciprocating hub 85 is activated to impose a rocking motion to the device 11. This distilled or deionized water is removed from first compartment 23 by rotating the turntable 75. If the test strip 37 is washed again with deionized water, fluid in the second compartment 25 is withdrawn by pipette from depression 59, and the step is repeated.

The test strip 37 is spun dry by rotating the device 11 about turntable 75 under slightly elevated temperatures. Preferably, the test strip 37 is read within three hours of drying. Turning now to FIG. 4, the test strip 37 is illuminated by light sources 39a and b. A suitable camera or film means 43 is calibrated and used to read and record the test strip 37 results. Illumination of the first chamber 21 by light emitting sources 39a or b produces consistent results because of the uniform dispersion of light entering chamber 21 by matte or colored wall surfaces associated with the chamber.

The present invention features a device capable of using a single test strip 37 and carrying the test strip 37 through a plurality of process steps. The device 11 is capable of being molded as a single piece, decreasing the cost of performing an assay. In addition, the device 11 can be cleaned and recycled for sequential use in a plurality of assays.

Thus, the present invention has been described with respect to preferred embodiments, which embodiments are capable of modification and alteration. The present invention should not be limited to the description provided, but should encompass such alterations and modifications as fall within the purview of the following claims.

We claim:

1. A vessel for processing fluids by moving in a first movement pattern, said first movement pattern comprising a stationary position and rotation in a circle, said circle having an axis, radius and a plane of rotation and a second movement pattern comprising a stationary position and a rocking motion, said vessel comprising a unitary molded housing having pivoting means and a single chamber, said pivoting means for imposing a second movement pattern on said vessel, said chamber having a first compartment, a second compartment and a single opening extending substantially the length of said first and second compartments, said first compartment having one or more walls defining a cavity for holding a fluid, said second compartment having one or more walls defining a cavity for holding a fluid, at least one of said one or more walls of said first compartment and at least one of said one or more walls of said second compartment comprising weir means interposed between said first and second compartment defining a first fluid retention area in said first compartment to hold liquid when said vessel is in said stationary position and a passage within said chamber for fluid when said vessel is rotated, said second compartment having at least one of said one or more walls defining a second fluid retention area for holding fluid when said vessel is in a stationary position and a third fluid retention area when said housing is rotated, said vessel for receiving fluid in said first compartment and releasing said fluid upon rotation of said housing through said passage into said second compartment at least one or more walls of said first compartment and at least one or more walls of said second compartment comprising said opening and said opening allowing access to said first and second compartments.

2. The vessel of claim 1 wherein said weir means comprises at least one fluid transporting surface, said fluid transporting surface having an angle, measured from within the chamber from said plane of rotation to said surface, which is greater than 90° for promoting fluid movement on said surface by surface tension and preventing aerosol formation.

3. The vessel of claim 1 wherein said first compartment has at least one wall said wall receiving a flat, planar test strip.

4. The vessel of claim 3 wherein said test strip has immunological or nucleic acid probes and at least one flat planar surface of said test strip exposed to said opening.

5. The vessel of claim 1 wherein said pivoting means comprise tabs projecting from the housing for supporting said housing and allowing rotation about a pivoting arc.

6. The vessel of claim 1 wherein said housing is received on a turntable.

7. The vessel of claim 6 wherein said turntable has notches and said housing comprises tabs projecting from the housing, wherein said tabs are received in said notches.

8. The vessel of claim 7 wherein said turntable has second movement pattern means for imparting a second movement and said housing comprises arm means for engaging a second movement pattern.

9. The vessel of claim 8 wherein said second movement pattern means comprising a reciprocating hub, said hub moving perpendicular to said plane of rotation, said housing comprises an arm means for engaging said hub to rock said housing in a pivoting motion.

10. The vessel of claim 1 wherein said first compartment receives light and said one or more walls comprises light diffusing surface.

11. The vessel of claim 1 wherein said first compartment receives light and said one or more walls comprises light absorbing surface.

12. The vessel of claim 1 wherein said first compartment has a bottom planar surface, two opposing side walls, an axial wall and a weir wall, said weir wall comprising weir means, said two side walls having an first angle with respect to said bottom wall, said first angle is substantially equal to provide a symmetrical reflective light pattern and, said axial wall and said weir wall having a second angle with respect to said bottom wall, said second angle being substantially equal to provide a symmetrical reflective light pattern on said bottom wall.

13. The vessel of claim 1 wherein said second compartment has a depression in said one or more walls defining said second fluid retention area, for receiving fluids by gravity flow and for receiving pipettes and fluids withdrawing means to allow emptying of said second compartment.

14. The vessel of claim 1 wherein said third fluid retention area of second compartment comprises a back wall, wherein said back wall defines an angle with respect to the plane of rotation within the chamber, said angle is less than 90°.

15. The vessel of claim 1 wherein said second compartment has one or more walls extending laterally.

16. A method for processing fluids by moving fluid in a first movement pattern, said first movement pattern comprising a stationary position and rotation in a circle, said circle having an axis, radius and a plane of rotation and a second movement pattern comprising a stationary position and a rocking motion, wherein a pivoting means imposes said second movement pattern, comprising the following steps:

(a) placing fluids in a vessel comprising a housing having a chamber, said chamber having a first compartment and a second compartment, said first compartment having one or more walls defining a cavity for holding a fluid, said second compartment having one or more walls defining a cavity for holding a fluid, at least one of said one or more walls of said first compartment and at least one of said one or more walls of said second compartment comprising weir means interposed between said first and second compartment defining a fluid retention area in said first compartment to hold liquid when said vessel is in said stationary position and a passage within said chamber for fluid upon rotation of said vessel, said second compartment having at least one of said one or more walls defining a first fluid retention area for holding fluid when said vessel is in a stationary position and a second fluid retention area when said housing is rotated, said passage in fluid communication with said first and second compartment upon rotation of said housing, said vessel for receiving fluid in said first compartment and releasing said fluid upon rotation of said housing through said passage into said second compartment, b) imposing said rocking motion comprising a pivoting movement about a point along the radius to tilt or incline the housing with respect to the plane of rotation to promote mixing and distribution of fluids in said first or second compartment of said vessel; and c) imposing said first movement pattern on said vessel to move fluid from said first compartment to said second compartment through said passage and into said second fluid retention area of said second compartment when said vessel is rotated, and into said first fluid retention area of the second compartment when said vessel is stationary in the first movement pattern.

17. The method of claim 16 wherein said first compartment has at least one wall said wall receiving a flat, planar test strip.

18. The method of claim 16 wherein said first compartment comprises said test strip having immobilized immunological or nucleic acid probes and at least one planar surface of said test strip exposed to said opening.

19. The method of claim 18 wherein said first compartment receives light and said one or more walls comprises light diffusing surfaces, said method comprising the step of illuminating said first compartment and monitoring said test strip for the presence of analyte.

20. The method of claim 18 wherein said first compartment receives light and said one or more walls comprises light absorbing surface, said method comprising the step of illuminating said first compartment and monitoring said test strip for the presence of analyte.

21. The method of claim 16 wherein said second compartment has a back wall comprising said third fluid retention area, said back wall having an angle with respect to said plane of rotation, said angle measured within said chamber from said plane of rotation to said back walls is less than 90°.

22. The method of claim 16, wherein said first compartment has a bottom planar surface, two opposing side walls, an axial wall and a weir wall, said weir wall comprising weir means, said two side walls having a first angle with respect to said bottom wall, said angle is substantially equal to provide a symmetrical reflective light pattern, said axial wall and said weir wall having a second angle with respect to said bottom wall, said second angle being substantially equal to provide a symmetrical reflective light pattern on said bottom wall.

* * * * *